United States Patent [19]

Miyazawa et al.

[11] Patent Number: 4,818,432
[45] Date of Patent: Apr. 4, 1989

[54] 3-SUBSTITUTED BIPHENYL COMPOUND

[75] Inventors: Kazutoshi Miyazawa; Takashi Inukai; Hiromichi Inoue; Shinichi Saito; Kouji Ohno, all of Kanagawa, Japan

[73] Assignee: Chisso Corporation, Ohsaka, Japan

[21] Appl. No.: 42,805

[22] Filed: Apr. 27, 1987

[30] Foreign Application Priority Data

Apr. 25, 1986 [JP] Japan .................................. 61-90618

[51] Int. Cl.[4] .................... C09K 19/12; C07C 49/807; C07C 43/225; C07C 49/84
[52] U.S. Cl. ........................... 252/299.66; 252/299.01; 350/350 S; 558/415; 558/428; 568/331; 568/642
[58] Field of Search ........... 252/299.66, 299.5, 299.01; 350/350 S; 558/415, 423; 568/331, 642

[56] References Cited

U.S. PATENT DOCUMENTS

| 4,138,359 | 2/1979 | Mizukuchi et al. | 252/299.65 |
|---|---|---|---|
| 4,216,109 | 8/1980 | Mizukuchi et al. | 252/299.65 |
| 4,478,740 | 10/1984 | Eidenschink et al. | 252/299.66 |
| 4,490,305 | 12/1984 | Eidenschink et al. | 252/299.66 |
| 4,505,838 | 3/1985 | Romer et al. | 252/299.66 |
| 4,536,321 | 8/1985 | Sugimori et al. | 252/299.63 |
| 4,544,771 | 2/1985 | Romer et al. | 568/331 |
| 4,614,609 | 9/1986 | Inoue et al. | 252/299.66 |

FOREIGN PATENT DOCUMENTS

| 84194 | 7/1984 | European Pat. Off. | 252/299.66 |
|---|---|---|---|
| 188222 | 7/1986 | European Pat. Off. | 252/299.65 |
| 80-47642 | 4/1980 | Japan | 252/299.65 |
| 80-81849 | 6/1980 | Japan | 252/299.65 |
| 82-77644 | 5/1982 | Japan | 252/299.63 |

OTHER PUBLICATIONS

Gray et al., Liquid Crystals & Plastic Crystals, vol. 1, pp. 142-143 (1973).
Osman et al., Z. Naturforsch., vol. 38B, pp. 1221-1226, (1983).

Primary Examiner—Teddy S. Gron
Assistant Examiner—J. E. Thomas
Attorney, Agent, or Firm—Wenderoth, Lind & Ponack

[57] ABSTRACT

A novel 3-substituted biphenyl compound useful as a component of chiral liquid crystal compositions useful for light-switching elements by the use of ferroelectric liquid crystals; a chiral liquid crystal composition containing the compound; and a light-switching element utilizing the composition are provided, which compound is expressed by the formula

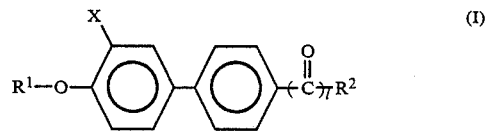

wherein either one of $R^1$ or $R^2$ represents an alkyl group of 4 to 18 carbon atoms having a methyl branch and the other thereof represents an alkyl group of 2 to 18 carbon atoms; X represents a halogen atom of F, Cl or Br or cyano group; and l represents 0 to 1.

2 Claims, No Drawings

3-SUBSTITUTED BIPHENYL COMPOUND

BACKGROUND OF THE INVENTION

1. Field of the Invention

This invention relates to a novel organic compound and a liquid crystal composition containing the same, and more particularly it relates to a biphenyl compound useful as a component of chiral smectic liquid crystal compositions useful for light switching elements by the use of ferroelectric liquid crystals.

2. Description of the Prior Art

Among liquid crystal display elements, those of the twisted nematic (TN) type display mode have currently been most widely used, but they are inferior in response rate to emissive type display elements (e.g. electroluminescence, plasma display, etc.), and various improvements in this respect have been attempted, but it appears, nevertheless, that the possibility of notable improvement has not been achieved. Thus, various liquid crystal display devices based on a different principle from that of TN type display elements have been tried in place thereof. Among these devices, there is a device of display mode utilizing ferroelectric liquid crystals (N. A. Clark et al, Applied Phys. lett., 36, 899 (1980)). This mode utilizes the chiral smectic C phase (hereinafter abbreviated to SC* phase), the chiral smectic H phase (hereinafter abbreviated to SH* phase) or the like of ferroelectric liquid crystals, and liquid crystal substances having such phases in the vicinity of room temperature have been desired as those suitable to this mode.

Now, ferroelectric display elements utilizing SC* phase have the following three superior specific features as compared with TN mode display elements.

The first specific feature is that the display elements reply at a very high rate so that the response time is 1/100 or less of those of conventional TN mode display elements. The second specific feature is that there is a memory effect so that the multiplex drive is easy in combination thereof with the above high rate response properties. The third specific feature is that when the gray scale is given in the case of TN display mode, this is effected by adjusting the impressed voltage, but there are raised difficult problems such as temperature dependency of threshold voltage, temperature dependency of response rate, etc.; whereas when the light-switching effect of SC* phase is applied, it is possible to readily obtain the gray scale by adjusting the reverse time of polarity and hence the display elements are very suitable to graphic display.

However, in spite of such superior specific features, the SC* phase region of currently known chiral smectic compositions is still insufficient particularly at its lower temperature part. Hence, in the aspect of practical use, too, liquid crystal substances covering the lower temperature region have been desired. Thus, the present inventors noted biphenyl compounds having a liquid crystal region at relatively low temperatures. However, most of the generally known biphenyl liquid crystal substances often have smectic phases as shown below other than SC phase and hence it has raised a problem to use such substances as a component for chiral smectic compositions (Demus. D et al, J. Phys. Coll. 36, 349 (1975)).

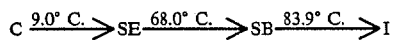

Thus, the present inventors have made extensive research on biphenyl compounds substituted by a halogen atom at the 3-position thereof, and as a result have found that the compounds exhibit superior specific features when they are used as a component for chiral smectic liquid crystal compositions.

SUMMARY OF THE INVENTION

The present invention resides in a 3-substituted biphenyl compound expressed by the formula

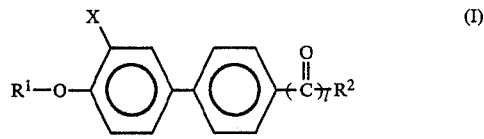

wherein either one of $R^1$ or $R^2$ represents an alkyl group of 4 to 18 carbon atoms having a methyl branch and the other thereof represents an alkyl group of 2 to 18 carbon atoms; X represents a halogen atom of F, Cl or Br or a cyano group; and l represents 0 or 1, and a chiral smectic liquid crystal composition containing at least one kind of the same.

DETAILED DESCRIPTION OF PREFERRED IMPROVEMENTS

The compound of the formula (I) includes optically active substances based on the methyl branch and racemic substances thereof, and both of these have common advantages when they are used as a component for chiral smectic compositions. Further, as shown later, the compound of the formula (I) includes those exhibiting smectic liquid crystalline phases by themselves and those not exhibiting them, but both of these have the same effectiveness when they are used as a chiral smectic component.

The values of physical properties (phase transition points) of representative examples of the compound of the formula (I) are shown in Table 1.

TABLE 1

| Sample No. | In formula (I) $R^1$ | $R^2$ | X | l | Absolute stereochemical configuration | Phase transition point (°C.) C | SC* | SA | I | Note |
|---|---|---|---|---|---|---|---|---|---|---|
| 1 | CH$_3$<br>\|<br>C$_2$H$_5$CH$-$(CH$_2$)$_2$ | C$_{12}$H$_{25}-$ | F | 0 | S | • 52.2 | — | — | • | |

TABLE 1-continued

| Sample No. | In formula (I) R¹ | R² | X | l | Absolute stereo-chemical configuration | Phase transition point (°C.) C | SC* | SA | I | Note |
|---|---|---|---|---|---|---|---|---|---|---|
| 2 | CH₃\|C₂H₅CH*–(CH₂)₃– | C₈H₁₇– | F | 0 | S | • 36.2 | — | — | • | |
| 3 | CH₃\|C₂H₅CH*–(CH₂)₃– | C₁₀H₂₁– | F | 0 | S | • 44.4 | — | — | • | |
| 4 | CH₃\|C₂H₅CH*–(CH₂)₄– | C₈H₁₇– | F | 0 | S | • 30.0 | — | — | • | |
| 5 | CH₃\|C₂H₅CH*–(CH₂)₄– | C₁₀H₂₁– | F | 0 | S | • 40.1 | — | — | • | |
| 6 | CH₃\|C₂H₅CH*–(CH₂)₄– | C₁₂H₂₅– | Br | 0 | S | • 11.0 | — | — | • | |
| 7 | CH₃\|C₂H₅CH*–(CH₂)₄– | C₁₂H₂₅– | CN | 0 | S | • 10.5 | — | — | • | |
| 8 | CH₃\|C₂H₅CH*–(CH₂)₅– | C₅H₁₁– | F | 0 | S | • 19.2 | (• 17.1) | • 28.1 | • | |
| 9 | CH₃\|C₂H₅CH*–(CH₂)₅– | C₈H₁₇– | F | 0 | S | • 33.4 | (• 30.8) | • 37.3 | • | |
| 10 | CH₃\|C₂H₅CH*–(CH₂)₅– | C₈H₁₇– | Br | 0 | S | • 29.5 | • 69.6(SX) | — | • | |
| 11 | CH₃\|C₂H₅CH*–(CH₂)₅– | C₈H₁₇– | CN | 0 | S | • 27.4 | — | • 31.1 | • | |
| 12 | CH₃\|C₂H₅CH*–(CH₂)₅– | C₁₀H₂₁ | F | 0 | S | • 39.0 | — | • 40.6 | • | |
| 13 | CH₃\|C₂H₅CH*–(CH₂)₅– | C₁₂H₂₅ | F | 0 | S | • 43.5 | — | — | • | |
| 14 | CH₃\|C₂H₅CH*–(CH₂)₅– | C₁₂H₂₅ | Cl | 0 | S | • 20.6 | — | — | • | |
| 15 | CH₃\|C₂H₅CH*–(CH₂)₆– | C₈H₁₇– | F | 0 | S | • 31.2 | (• 25.0) | • 35.4 | • | |
| 16 | CH₃\|C₂H₅CH*–(CH₂)₆– | C₁₀H₂₁– | F | 0 | S | • 32.5 | (• 30.1) | • 39.5 | • | Exp.1 |
| 17 | CH₃\|C₂H₅CH*–(CH₂)₇– | C₅H₁₁– | F | 0 | S | • 19.0 | (• 11.4) | • 32.3 | • | |

TABLE 1-continued

| Sample No. | In formula (I) R¹ | R² | X | l | Absolute stereochemical configuration | Phase transition point (°C.) C | SC* | SA | I | Note |
|---|---|---|---|---|---|---|---|---|---|---|
| 18 | $CH_3$ <br> $C_2H_5\overset{*}{C}H\text{---}(CH_2)_7\text{---}$ | $C_{12}H_{25}\text{---}$ | F | 0 | S | • 46.3 | (• 41.5) | • 46.8 | • | |
| 19 | $CH_3$ <br> $C_6H_{13}\overset{*}{C}H\text{---}$ | $C_{12}H_{25}$ | Br | 0 | S | • −32.5 | — | — | • | |
| 20 | $CH_3$ <br> $C_6H_{13}\overset{*}{C}H\text{---}$ | $C_{12}H_{25}$ | CN | 0 | S | • −17.8 | — | — | • | |
| 21 | $C_8H_{17}\text{---}$ | $CH_3$ <br> $C_2H_5\overset{*}{C}H\text{---}(CH_2)_2\text{---}$ | F | 0 | S | • 30.5 | — | — | • | |
| 22 | $C_9H_{19}\text{---}$ | $CH_3$ <br> $C_2H_5\overset{*}{C}H\text{---}(CH_2)_2\text{---}$ | F | 0 | S | • 31.5 | — | — | • | |
| 23 | $C_{12}H_{25}\text{---}$ | $CH_3$ <br> $C_2H_5\overset{*}{C}H\text{---}(CH_2)_2\text{---}$ | F | 0 | S | • 38.0 | — | — | • | |
| 24 | $C_{10}H_{21}\text{---}$ | $CH_3$ <br> $C_2H_5\overset{*}{C}H\text{---}(CH_2)_5\text{---}$ | F | 0 | S | • 25.4 | • 30.5 | • 33.6 | • | |
| 25 | $C_{12}H_{25}\text{---}$ | $CH_3$ <br> $C_2H_5\overset{*}{C}H\text{---}(CH_2)_5\text{---}$ | F | 0 | S | • 35.3 | (• 33.3) | • 36.7 | • | |
| 26 | $C_7H_{15}\text{---}$ | $CH_3$ <br> $C_2H_5\overset{*}{C}H\text{---}(CH_2)_5\text{---}$ | Br | 0 | S | • −20.0 | — | — | • | |
| 27 | $C_7H_{15}\text{---}$ | $CH_3$ <br> $C_2H_5\overset{*}{C}H\text{---}(CH_2)_5\text{---}$ | CN | 0 | S | • 5.0 | — | • 26.4 | • | |
| 28 | $CH_3$ <br> $C_2H_5\overset{*}{C}H\text{---}(CH_2)_2\text{---}$ | $C_8H_{17}$ | F | 1 | S | • 85.0 | — | • 100.0 | • | |
| 29 | $CH_3$ <br> $C_2H_5\overset{*}{C}H\text{---}(CH_2)_3\text{---}$ | $C_8H_{17}$ | F | 1 | S | • 82.4 | — | • 105.6 | • | |
| 30 | $CH_3$ <br> $C_2H_5\overset{*}{C}H\text{---}(CH_2)_4\text{---}$ | $C_8H_{17}$ | F | 1 | S | • 80.6 | — | • 102.0 | • | |
| 31 | $CH_3$ <br> $C_2H_5\overset{*}{C}H\text{---}(CH_2)_5\text{---}$ | $C_8H_{17}\text{---}$ | F | 1 | S | • 74.5 | • 77.4 | • 107.3 | • | |
| 32 | $CH_3$ <br> $C_2H_5\overset{*}{C}H\text{---}(CH_2)_5\text{---}$ | $C_9H_{19}\text{---}$ | Br | 1 | S | • 44.5 | • 51.8 | • 81.8 | • | |
| 33 | $CH_3$ <br> $C_2H_5\overset{*}{C}H\text{---}(CH_2)_5\text{---}$ | $C_9H_{19}\text{---}$ | CN | 1 | S | • 47.0 | • 71.2 | • 99.3 | • | |

TABLE 1-continued

| Sample No. | In formula (I) R¹ | R² | X | l | Absolute stereochemical configuration | Phase transition point (°C.) C | SC* | SA | I | Note |
|---|---|---|---|---|---|---|---|---|---|---|
| 34 | CH₃<br>\|<br>C₂H₅CH—(CH₂)₅<br>* | C₁₁H₂₃— | F | 1 | S | • 68.5 | • 88.2 | • 103.5 | • | |
| 35 | CH₃<br>\|<br>C₂H₅CH—(CH₂)₅<br>* | C₁₁H₂₃ | Cl | 1 | S | • 45.2 | • 67.4 | • 86.6 | • | |
| 36 | CH₃<br>\|<br>C₂H₅CH—(CH₂)₇<br>* | C₈H₁₇ | F | 1 | S | • 81.7 | — | ○ 107.6 | • | |
| 37 | CH₃<br>\|<br>C₂H₅CH—(CH₂)₇<br>* | C₁₁H₂₃ | F | 1 | S | • 68.0 | • 87.4 | • 103.0 | • | Exp.2 |
| 38 | C₇H₁₅— | CH₃<br>\|<br>C₂H₅CHCH₂—<br>* | F | 1 | S | • 91.1 | — | — | • | |
| 39 | C₈H₁₇— | CH₃<br>\|<br>C₂H₅CHCH₂—<br>* | F | 1 | S | • 84.1 | — | — | • | |
| 40 | C₁₀H₂₁— | CH₃<br>\|<br>C₂H₅CH(CH₂)₂<br>* | F | 1 | S | • 72.6 | — | • 78.3 | • | |
| 41 | C₈H₁₇— | CH₃<br>\|<br>C₂H₅CH(CH₂)₄<br>* | F | 1 | S | • 46.0 | • 68.0 | • 94.2 | • | |
| 42 | C₁₀H₂₁— | CH₃<br>\|<br>C₂H₅CH(CH₂)₄<br>* | F | 1 | S | • 44.8 | • 60.8 | • 91.2 | • | |
| 43 | C₁₂H₂₅ | CH₃<br>\|<br>C₂H₅CH(CH₂)₄<br>* | F | 1 | S | • 45.5 | • 50.0 | ○ 87.5 | • | |
| 44 | CH₃<br>\|<br>C₂H₅CH—(CH₂)₅<br>* | C₈H₁₇— | F | 0 | racemate | • 32.0 | (• 28.8) | ○ 36.7 | • | |
| 45 | CH₃<br>\|<br>C₂H₅CH—(CH₂)₅<br>* | C₁₀H₂₁— | F | 0 | racemate | • 39.3 | — | • 40.0 | • | |

When the compound of the formula (I) of the present invention is used as a chiral smectic component for chiral smectic liquid crystal compositions, there is a tendency that liquid crystalline phases other than SA phase and SC* phase of the compositions and having a higher degree of order than those of the latter phases are difficult to be formed; hence the compound has a superior specific feature of covering the lower temperature region of chiral smectic compositions.

Further, another greater specific feature of biphenyl compounds consists in its low viscosity. As described above, a great advantage of display elements making use of chiral liquid crystal compositions consists in that the response rate is high, that is, the time during which molecules are reversed by applying an electric field is short. Thus, even in view of the fact that the low viscosity does not hinder the reversal, it can be said that the biphenyl compound of the present invention has superior specific features when it is used as a component for chiral smectic liquid crystal compositions, to those of other liquid crystal compounds such as ester liquid crystal compounds.

When the compound of the present invention is used as a component for chiral smectic liquid crystal compositions, other chiral smectic compounds are necessarily required to use together, but there is no particular limitation as to the kind of these compounds.

In addition, among the compounds of the formula (I), optically active substances have an optically active carbon atom; hence when such substances are added to nematic liquid crystal(s), nematic liquid crystal compositions having a capability of inducing a twisted structure are obtained. Since nematic liquid crystal i.e., chiral nematic liquid crystal compositions, do not form the so-called reverse domain of TN type display elements, it is possible to use the compound of the formula (I) as an agent for preventing the reverse domain from forming.

Among the compounds of the formula (I), those wherein l represents zero and X represents a halogen atom of F or Cl may be prepared through the following passageways:

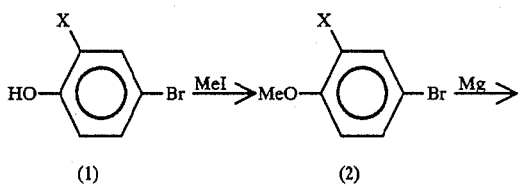

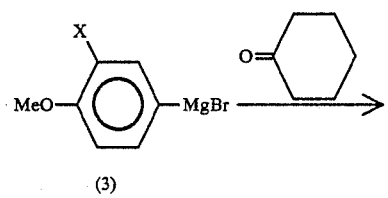

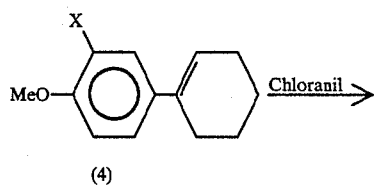

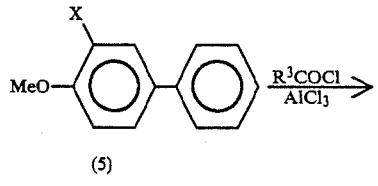

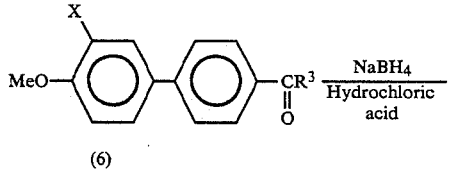

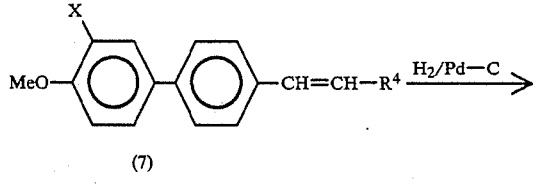

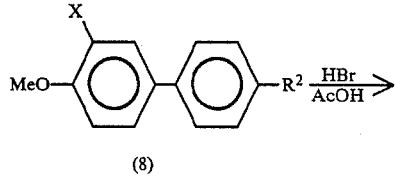

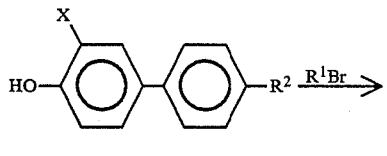

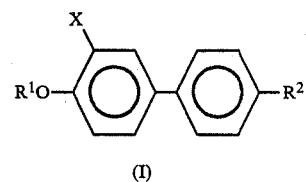

wherein $R^3$ represents an alkyl group having a carbon number less by one than that of $R^2$ and $R^4$ represents an alkyl group having a carbon number less by one than that of $R^3$.

Namely, a known 2-halogeno-4-bromophenol(1) is subjected to methyl etherification, followed by reacting the resulting compound with Mg to prepare a Grignard reagent (3), reacting this reagent with cyclohexanone to prepare a compound (4), dehydrogenating this compound (4) to prepare a compound (5), subjecting this compound (5) to Friedel-Crafts acylation reaction in the presence of anhydrous aluminum chloride as catalyst, reducing the resulting compound (6) with $NaB_4$ to prepare an alcohol, dehydrating this alcohol to prepare a compound (7), reducing this compound (7) in the presence of Pd/C catalyst to introduce an alkyl group, reacting the resulting compound (8) with hydrobromic acid to prepare a compound (9) and subjecting this compound to etherification according to a known method to obtain the objective compound of the formula (I).

Further, compounds of the formula (I) wherein l represents zero and X represents Br or CN group may be suitably prepared through the following passageways:

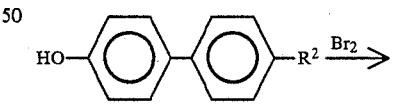

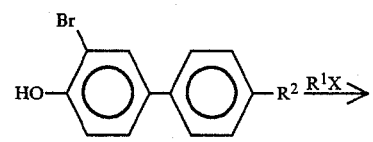

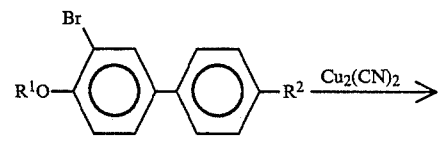

-continued

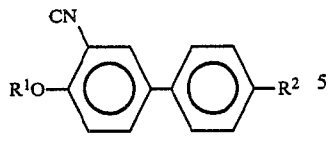

(I) (l = 0, X = CN)

In the above passageways, the bromination in the first step is preferably carried out in p-dioxane and It is possible to reverse the order of the etherification in the second step and the cyano substitution reaction in the third step.

Further, compounds of the formula (I) wherein l represents 1 and X represents F, Cl or Br may be suitably prepared from the above compound (6) through the following passageways wherein, however, compound having replaced $R^2$ of the above compound (6) by $R^3$ is referred to as (6'):

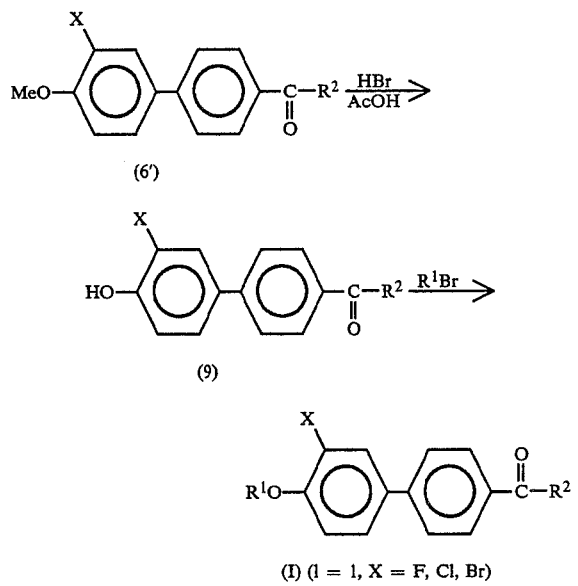

Further, compounds of the formula (I) wherein l represents 1 and X represents CN may be prepared as follows:

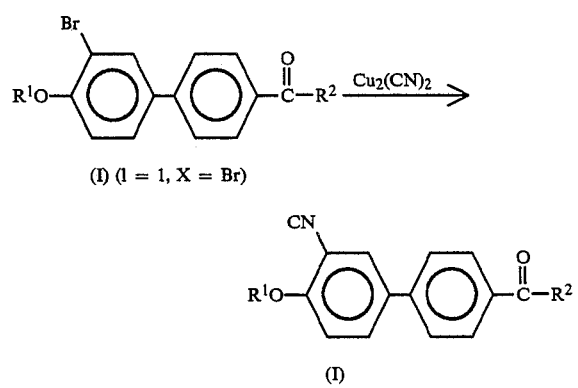

In addition, in any of the above cases, if either one of $R^1Br$, $R^3COCl$ or

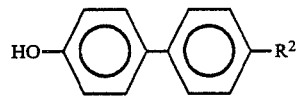

each as the raw material for introducing $R^1$ or $R^2$ is an optically active substance, the resulting compound of the formula (I) is also an optically active substance, while if a racemic substance is used as the raw material, the resulting objective substance is also a racemic substance. Further, as to the optically active substance and the racemic substance corresponding thereto, both the substances exhibit almost the same phase transition points except that the racemic substance exhibit no chiral property.

The compounds of the present invention and the liquid crystal compositions containing the same will be described below in more detail by way of Examples.

EXAMPLE 1

Preparation of optically active (S)-3-fluoro-4-(7''-methylnonyloxy)-4'-decylbiphenyl (a compound of the formula (I) wherein

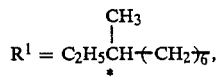

$R^2=C_{10}H_{21}$ and X=F; sample No. 16)

(i) Preparation of 3-fluoro-4-methoxybiphenyl

2-Fluoro-4-bromophenol (1) (382.0 g, 2.0 mols) was dissolved in ethanol (1,000 ml), followed by adding potassium hydroxide (113.0 g, 2.0 mols) to the solution, sufficiently agitating the mixture, dropwise adding thereto methyl iodide (312.3 g, 2.2 mols), refluxing it for 4 hours, distilling off most of the ethanol, distilling the residue under reduced pressure and collecting a fraction of 65°–66° C. (4.5 mmHg) to obtain 2-fluoro-4-bromoanisole (2) (328.0 g). This compound was reacted with Mg (38.9 g) in diethyl ether to obtain 3-fluoro-4-methoxyphenylmagnesium bromide (3), followed by dropwise adding thereto cyclohexanone (157.0 g, 1.6 mol) at 7° C. or lower, agitating the mixture at room temperature for about 30 minutes, adding thereto 6N—HCl (350 ml), refluxing the mixture for one hour, washing the resulting organic layer with water, distilling off diethyl ether and recrystallizing the residue from ethanol to obtain (3'-fluoro-4'-methoxyphenyl)-cyclohexene-1 (4) (180.4 g) having a m.p. of 49.0°–50.0° C. This compound (112.0 g, 0.55 mol) was dissolved in xylene (700 ml), followed by adding p-chloranil (267.0 g, 1.1 mol) to the solution, refluxing the mixture for 4 hours, filtering off the resulting tetrachlorohydroquinone, washing the filtrate with 2N—NaOH aqueous solution, distilling off the solvent, subjecting the residue to column chromatography with a column filled with activated alumina and recrystallizing the resulting material from ethanol to obtain 3-fluoro-4-methoxybiphenyl (5) (69.2 g) having a m.p. of 84.5°–86.0° C.

(ii) Preparation of 3-fluoro-4-hydroxy-4'-decylbiphenyl

3-Fluoro-4-methoxybiphenyl (60.0 g, 0.3 mol) obtained in the above step (i) and n-decanoyl chloride (60.0 g, 0.3 mol) were dissolved in carbon disulfide (420 ml), followed by dropwise addition of the solution into anhydrous aluminum chloride (42.0 g) in carbon disulfide at 10° C. or lower, heating the mixture for about one hour, adding 6N—HCl (60 ml), distilling off carbon disulfide, filtering off deposited crystals and recrystallizing them from ethyl acetate to obtain 3-fluoro-4-methoxy-4'-nonylcarbonylbiphenyl (6) (87.9 g). This compound (86.7 g, 0.24 mol) was added to isopropyl alcohol (900 ml), followed by all at once adding to the mixture, sodium borohydride (6.9 g, 0.18 mol) with stirring, refluxing the mixture for 30 minutes, adding 6N—HCl (360 ml), further refluxing the mixture for one hour, distilling off isopropyl alcohol, dissolving the residue in toluene sufficiently washing the solution with water, distilling off toluene, and hydrogenating the residue (containing compound (7)) as it is, in the presence of palladium-carbon to obtain 3-fluoro-4-methoxy-4'-decylbiphenyl (8) (58.8 g). This compound (58.8 g) was dissolved in acetic acid (1,200 ml), adding 47% hydrobromic acid (360 g) to the solution, refluxing the mixture for 20 hours, introducing it into water, filtering off deposited crystals and recrystallizing them from acetic acid to obtain 3-fluoro-4-hydroxy-4'-decylbiphenyl (8) (39.3 g) having a m.p. of 101.6°–102.3° C.

(iii) Preparation of the captioned compound

3-Fluoro-4-hydroxy-4'-decylbiphenyl (8.0 g, 0.024 mol) obtained in the above step (ii) was dissolved in methanol (50 ml), followed by adding potassium hydroxide (0.57 g, 0.026 mol) to the solution, agitating the mixture for a while, adding thereto optically active (S)-7-methylnonyl bromide (5.75 g, 0.026 mol) prepared according to a known method, refluxing the mixture for 5 hours, distilling off the solvent and recrystallizing the residue from ethanol to obtain the objective (S)-3-fluoro-4-(7"-methylnonyloxy)-4'-decylbiphenyl (7.2 g). This product exhibited the following phase transition points: C-SA point 32.5° C., SA-I point 39.5° C. and SA-SC* point 30.1° C. Further its values of elementary analysis accorded well with its calculated values as follows:

|   | Observed values | Calculated values (in terms of $C_{32}H_{49}OF$) |
|---|---|---|
| C | 81.90% | 82.00% |
| H | 10.40% | 10.54% |
| F | 4.10% | 4.05% |

The values of the physical properties of other compounds of the formula (I) similarly obtained are shown in Table 1 together with those of the following Example 2.

EXAMPLE 2

Preparation of (S)-3-fluoro-4-(8'-methyldecyloxy)-4'-dodecanoylbiphenyl (a compound of the formula (I) wherein

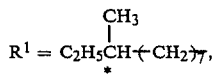

$R^2=C_{11}H_{23}-$, $l=1$ and $X=F$; sample No. 37)

Using dodecanoic acid chloride in place of decanoic acid chloride used in the step (ii) of Example 1, 3-fluoro-4-methoxy-4'-dodecanoylbiphenyl was obtained (m.p.: 124.0°–124.7° C.). This compound (30 g, 0.078 mol) was dissolved in acetic acid (260 ml), followed by adding to the solution, 47% hydrobromic acid (134 g), refluxing the mixture for 30 hours, introducing it into water, collecting deposited crystals and recrystallizing them from toluene to obtain 3-fluoro-4-hydroxy-4'-dodecanoylbiphenyl (19 g) having a m.p. of 123.2°–123.9° C.

This compound (5 g, 0.014 mol) was dissolved in methanol (100 ml), followed by adding potassium hydroxide (0.9 g, 0.016 mol) to the solution and then S-8-methyldecyl bromide (3.8 g, 0.016 mol), refluxing the mixtue for 4 hours, adding water and toluene, sufficiently agitating the mixture, sufficiently washing the resulting organic layer with 2N—NaOH aqueous solution, drying it over anhydrous magnesium sulfate, distilling off the solvent and recrystallizing the residue from ethanol to obtain S-3-fluoro-4-(8'-methyldecyloxy)-4'-dodecanoylbiphenyl (4.9 g).

This compound exhibited the following phase transition points: C-SC* point 68.0° C., SC*-SA point 87.4° C. and SA-I point 103.0° C. Further, its values of elementary analysis accorded well with its calculated values as follows:

|   | Observed values | Calculated values (in terms of $C_{35}H_{53}O_2F$) |
|---|---|---|
| C | 80.00% | 80.10% |
| H | 10.10% | 10.18% |
| F | 3.7% | 3.62% |

The values of physical properties of other compounds of the formula (I) similarly obtained wherein $l=1$ are shown in Table 1.

EXAMPLE 3 (USE EXAMPLE)

A liquid crystal composition consisting of the following compounds of the present invention listed in Table 1 was prepared:

| sample No. 16 | 40% by weight |
| sample No. 15 | 30% by weight and |
| sample No. 9 | 30% by weight. |

The above liquid crystal composition had a m.p. of 20.6° C., and exhibited SC* phase on the higher temperature side and SA phase at 26.7° C. and formed an isotropic liquid at 37.3° C.

To 60% by weight of the above liquid crystal composition were added the following chiral smectic liquid crystal compounds each in 20% by weight to prepare a chiral smectic liquid crystal composition:

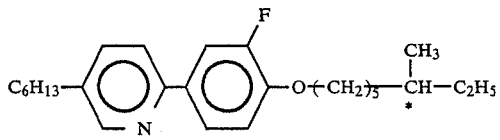

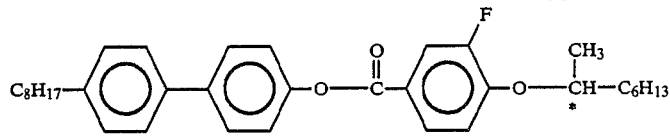

The resulting composition was filled in a cell of 2 μm thick provided with transparent electrodes, each obtained by applying PVA (polyvinyl alcohol) as an aligning agent onto the surface thereof and then subjecting the resulting surface to parallel aligning treatment. The resulting liquid crystal element was provided between two sheets of crossed polarizers and a voltage of 15 V was impressed to observe change in the intensity of transmitted light.

The response time was sought from the change in the intensity of transmitted light to give about 150μ sec at 25° C.

The above liquid crystal composition had a m.p. of −4.0° C., and exhibited SC* phase on the higher temperature side and SA phase at 40.2° C. and formed an isotropic liquid at 44.8° C. Its supercooled state was confirmed down to −9.0° C. and the composition exhibited SC* phase as far as this temperature and also no other smectic phases were observed.

In addition, the value of spontaneous polarization was 14 nC/cm$^2$ at 25° C. and the value of tilt angle was 22° at 25° C.

As described above, it is seen that when optically active liquid crystal compound(s) are mixed with the compound(s) of the formula (I) of the present invention, a ferroelectric chiral smectic liquid crystal composition having superior response properties is obtained.

What we claim is:

1. A chiral smectic c liquid crystal compound selected from the group consisting of
4'-(6-methyl-octyloxy)-3'-fluoro-4-pentylbiphenyl,
4'-(6-methyl-octyloxy)-3'-fluoro-4-octylbiphenyl,
4'-(7-methyl-nonyloxy)-3'-fluoro-4-octylbiphenyl,
4'-(7-methyl-nonyloxy)-3'-fluoro-4-decylbiphenyl,
4'-(8-methyl-decyloxy)-3'-fluoro-4-pentylbiphenyl,
4'-(8-methyl-decyloxy)-3'-fluoro-4-dodecylbiphenyl,
4'-decyloxy-3'-fluoro-4-(6-methyl-octyl)-biphenyl,
4'-dodecyloxy-3'-fluoro-4-(6-methyl-octyl)-biphenyl,
4'-(6-methyl-octyloxy)-3'-fluoro-4-nonanoyl-biphenyl,
4'-(6-methyl-octyloxy)-3'-bromo-4-decanoyl-biphenyl,
4'-(6-methyl-octyloxy)-3'-cyano-4-decanoyl-biphenyl,
4'-(6-methyl-octyloxy)-3'-fluoro-4-dodecanoyl-biphenyl,
4'-(6-methyl-octyloxy)-3'-chloro-4-dodecanoyl-biphenyl,
4'-(8-methyl-decyloxy)-3'-fluoro-4-dodecanoyl-biphenyl,
4'-octyloxyl-3'-fluoro-4-(6-methyl-octanoyl)-biphenyl,
4'-decycloxy-3'-fluoro-4-(6-methyl-octanoyl)-biphenyl, and
4'-dodecyloxy-3'-fluoro-4-(6-methyl-octanoyl)-biphenyl.

2. A chiral smectic C liquid crystal composition having at least two components at least one of which is a compound set forth in claim 1.

* * * * *